US008328358B2

(12) United States Patent
Sander

(10) Patent No.: US 8,328,358 B2
(45) Date of Patent: Dec. 11, 2012

(54) ILLUMINATION SYSTEM FOR AN OPHTHALMIC SURGICAL MICROSCOPE AND METHOD THEREOF

(75) Inventor: Ulrich Sander, Rebstein (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 106 days.

(21) Appl. No.: 13/090,864

(22) Filed: Apr. 20, 2011

(65) Prior Publication Data
US 2011/0261324 A1  Oct. 27, 2011

(30) Foreign Application Priority Data

Apr. 23, 2010 (DE) .......................... 10 2010 016 623

(51) Int. Cl.
*A61B 3/10* (2006.01)
*G02C 21/06* (2006.01)
(52) U.S. Cl. .......................... 351/221; 351/246; 359/385
(58) Field of Classification Search .................. 351/221, 351/246, 205; 359/385, 372, 389; 606/4, 606/5, 6; 607/53, 54
See application file for complete search history.

(56) References Cited

U.S. PATENT DOCUMENTS

| | | | | |
|---|---|---|---|---|
| 5,619,372 A | * | 4/1997 | Hellmuth et al. | 359/389 |
| 6,624,932 B2 | * | 9/2003 | Koetke | 359/389 |
| 7,839,566 B2 | * | 11/2010 | Andrews et al. | 359/385 |

FOREIGN PATENT DOCUMENTS

| | | |
|---|---|---|
| DE | 4028605 A1 | 3/1992 |
| DE | 9217517 U1 | 2/1993 |
| DE | 10202509 A1 | 7/2003 |
| DE | 102005042436 A1 | 4/2007 |

* cited by examiner

*Primary Examiner* — Hung Dang
(74) *Attorney, Agent, or Firm* — Patentbar International, P.C.

(57) ABSTRACT

Disclosed is an illumination system for an ophthalmic surgical microscope (10), including a light source (32) for emitting light along an illumination beam path (50) directed toward an eye (12) of a patient, and a measuring device (54, 62) for measuring a parameter of the patient's eye (12). The illumination system further includes an adjustable optical element (48) which allows the orientation of the illumination beam path (50) to be adjusted relative to an observation beam path (16L) of the surgical microscope (10) so as to obtain a red reflex, and a control device (60) which determines a red-reflex-optimized control parameter based on the measured parameter of the patient's eye (12) and adjusts the optical element (48) according to the red-reflex-optimized control parameter.

10 Claims, 4 Drawing Sheets

ILLUMINATION SYSTEM FOR AN OPHTHALMIC SURGICAL MICROSCOPE AND METHOD THEREOF

CROSS-REFERENCE TO RELATED APPLICATIONS

This Application claims priority to German Patent Application No. DE 10 2010 016 623.5 filed on Apr. 23, 2010, that is incorporated herein by reference in its entirety.

FIELD OF THE INVENTION

The present invention relates to an illumination system for an ophthalmic surgical microscope, including a light source for emitting light along an illumination beam path directed toward an eye of a patient, and a measuring device for measuring a parameter of the patient's eye. The present invention also relates to an ophthalmic surgical microscope, and to a method for operating an illumination system for an ophthalmic surgical microscope.

BACKGROUND OF THE INVENTION

In eye surgery, the illumination in an ophthalmic surgical microscope must often meet special requirements. For example, in cataract surgery, illumination systems are used which illuminate the patient's eye in such a way that the illumination beam path extends substantially coaxially with the observation beam path of the surgical microscope. This produces the so-called red reflex, in which the light scattered back from the retina causes the pupil of the patient's eye being operated on to shine with a reddish light. This red reflex illumination is advantageous, particularly in cataract surgery, because residual tissue, which may be left after the removal of the eye lens from the lens capsule and has to be removed to avoid complications, can be detected particularly easily against the backlight provided by the red reflex.

The red reflex seen by the operator is highly dependent on the individual characteristics of the patient's eye to be operated on. Experience shows that a patient's eye which is myopic and therefore relatively long provides a poorer red reflex than an eye which is hyperopic and therefore shorter. It is therefore advantageous if the illumination can be adapted to the individual characteristics of the patient's eye being operated on.

German Publication DE 92 17 517 U1 describes a surgical microscope having an illumination system which allows red reflex illumination of the lens capsule. In order to increase the contrast according to any possible ametropia of the patient, a lens, which was selected prior to surgery to match the ametropia of the eye, is swung in between the microscope objective and the patient's eye. However, this approach is relatively complex.

In German Patent Application DE 40 28 605 A1, an illumination system for an ophthalmic surgical microscope is described which includes a light source for emitting light along an illumination beam path directed toward an eye of a patient, as well as two deflection mirrors, each of which directs part of the illuminating light to the surgical area. One of the two deflection mirrors is adjustable to vary the angle at which the illuminating light deflected by it strikes the surgical area.

German Patent Application DE 10 2005 042 436 A1 describes an illumination system for an ophthalmic surgical microscope, including a light source for emitting light toward an eye of a patient, and a measuring device for measuring a parameter of the patient's eye. A model of the patient's eye is calculated based on the measured parameter. This model of the patient's eye is then displayed on a display device.

German Patent Application DE 102 02 509 A1 discloses an ophthalmic surgical microscope of the kind set forth in the preamble of claim 1, which uses a refractometer allowing parameters of the patient's eye being operated on to be determined in situ; i.e., during surgery. This enables the operator to take corrective measures during surgery, for example to minimize any detected residual ametropia.

SUMMARY OF THE INVENTION

It is an object of the present invention to provide an illumination system for a surgical microscope, which will allow the red reflex illumination to be optimized during eye surgery in a particularly easy way.

In an illumination system of the type specified at the outset, this object is achieved according to the present invention by an adjustable optical element which allows the orientation of the illumination beam path to be adjusted relative to an observation beam path of the surgical microscope so as to obtain a red reflex, and by a control device which determines a red-reflex-optimized control parameter based on the measured parameter of the patient's eye and adjusts the optical element according to this red-reflex-optimized control parameter.

The present invention provides an illumination system which allows the microscope illumination to be adapted to the individual characteristics of the patient's eye to be operated on to thereby optimize the red reflex. The illumination system of the present invention achieves this by using the measured parameter of the patient's eye to adjust the orientation of the illumination beam path relative to the observation beam path of the surgical microscope in a suitable manner by means of an optical element. To this end, the optical element is adjusted according to a control parameter which is determined based on the measured parameter of the patient's eye in such a way that the illumination beam path adjusted in its orientation according to this control parameter optimizes the red reflex seen by the operator.

The parameter of the patent's eye that is measured and used to optimize the red reflex may be any quantity which has a significant and predictable effect on the production of the red reflex. A unique relationship may then be established between such a quantity and the control parameter that can be used to control the adjustable optical element in a red-reflex-optimized manner. For example, the length of the patient's eye, or a quantity corresponding to this length, can be used an individual parameter, because the red reflex obtainable by the microscope illumination is highly dependent on the length of the eye. However, other parameters, such as quantities indicative of the refraction of the refractive media in the eye, may also be used to optimize the red reflex in accordance with the present invention.

Another advantage of the present invention is that it reduces the risk of damage to the patient's eye during illumination thereof as compared to known methods. In particular, when illuminating a patient's eye which is hyperopic and thus relatively short and, as experience shows, inherently provides a relatively good red reflex, it may be possible by suitable adjustment of the optical element to keep the illuminated retinal area (hereinafter also referred to as "illuminated area") away from the particularly light-sensitive macula without significantly reducing the quality of the red reflex. This may be achieved via a relationship empirically established, for example prior to surgery, between the measured parameter and the control parameter.

Preferably, the measuring device includes a measuring unit for measuring the parameter of the patient's eye in situ. Measuring the parameter in situ; i.e, during surgery, allows the illumination to be flexibly adapted to variations in the characteristics of the patient's eye during surgery. For example, the red reflex may change during cataract surgery upon removal of the eye lens from its capsule. If, in this case, an optical parameter reflecting this change is measured in situ, then the red reflex illumination can be adapted to the changed conditions.

Preferably, the measuring unit is a refractometer. However, the present invention is not limited to such a measuring unit. For example, a coherence interferometer, a skiascope or a keratometer may also be used as the measuring unit. All these measuring units are capable of measuring a parameter of the patent's eye which affects the red reflex.

As an alternative, or in addition to a measuring unit that operates in situ, the measuring device may also include an input device for inputting the ex-situ determined parameter of the patient's eye, as well as a memory unit for storing the parameter that has been input. In this case, the parameter of the patient's eye is measured prior to surgery, and is then used during the surgical procedure for adjusting the optical element based on the red-reflex optimized control parameter which corresponds to said [eye] parameter.

The optical element may for example be a mirror disposed in the illumination beam path. Such a minor allows the orientation of the illumination beam path to be easily and accurately adjusted relative to the observation beam path of the surgical microscope. However, other optical elements, such as lenses, diaphragms or filters, may also be used for adjusting the orientation of the illumination beam path. Moreover, instead of the adjustable optical element, the light source of the illumination system may also be used to adapt the illumination so as to obtain an optimized red reflex. For example, such adaptation may be performed based on the spectral condition of the emitted light.

Preferably, the control device includes an actuator unit which moves the minor along the illumination beam path. This allows easy and accurate adjustment of the orientation of the illumination beam path.

In another advantageous embodiment, the illumination system includes an output means for outputting an enable prompt requesting a user to enable adjustment of the optical element according to the determined red-reflex-optimized control parameter, as well as an input means by which the user enables adjustment of the optical element according to the determined red-reflex-optimized control parameter. This embodiment allows for particularly safe operation of the illumination system. For example, the optical element is adjusted to adapt the red reflex only if a user, usually the operator, enables such adjustment of the optical element upon verification. It is conceivable, for instance, that the control device could suggest an adjustment of the optical element which would result in the retinal area currently illuminated to be moved toward the particularly light-sensitive macula. In this case, if the operator decides that the not yet optimized red reflex is sufficiently effective, then he or she may refrain from optimizing the red reflex so as to prevent damage to the macula.

The present invention further provides an ophthalmic surgical microscope having an illumination system of the type described above, and a method for operating an illumination system for an ophthalmic surgical microscope.

BRIEF DESCRIPTION OF THE DRAWINGS

The present invention is described below with reference to an exemplary embodiment and the accompanying drawings, in which.

DETAILED DESCRIPTION OF THE PREFERRED EMBODIMENTS

Figure 1:
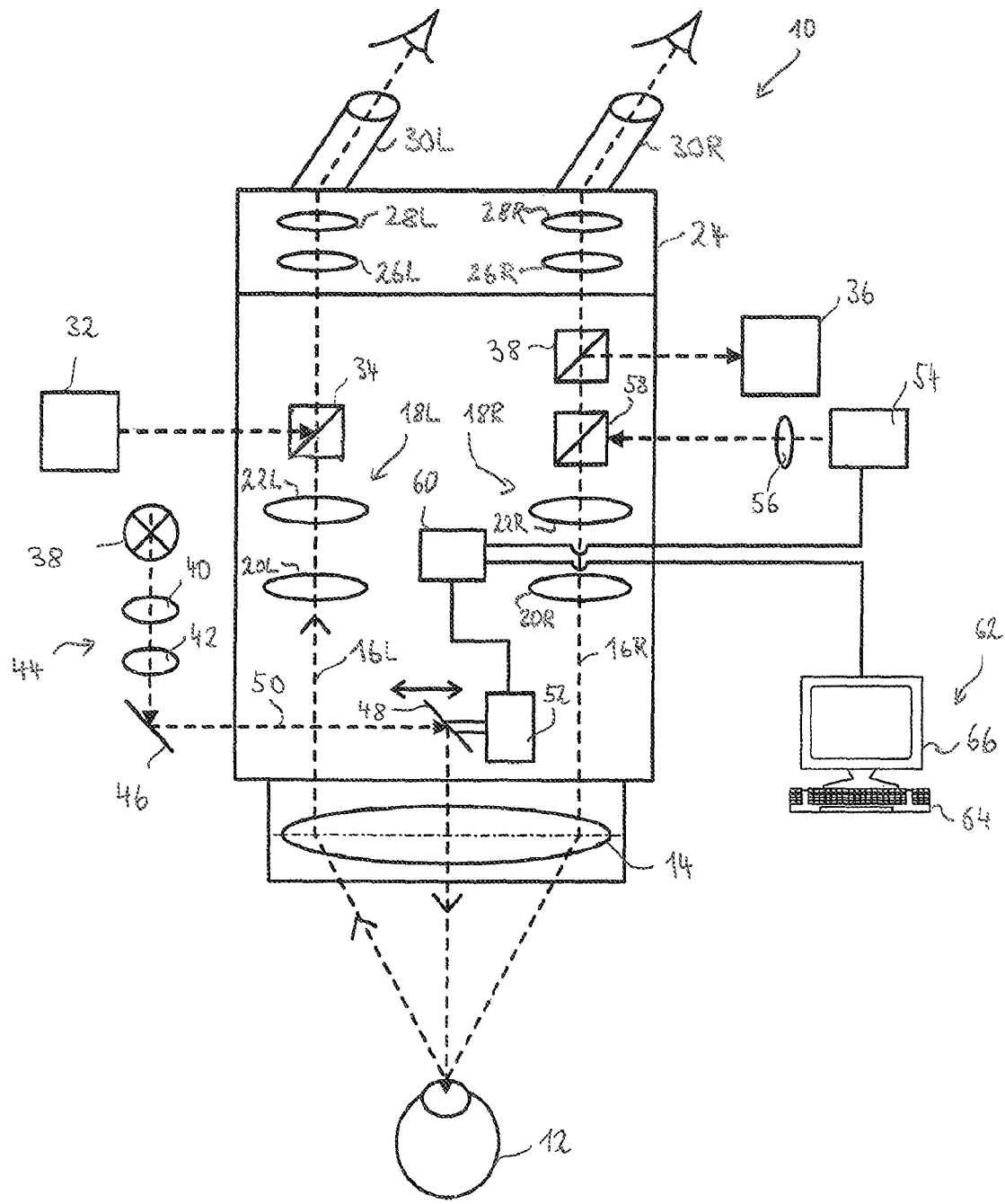
FIG. 1 is a schematic view of a stereoscopic ophthalmic microscope representing an exemplary embodiment [of the present invention]

FIG. 1 shows a stereoscopic ophthalmic microscope 10 which, in the present exemplary embodiment, is used to perform cataract surgery on a patient's eye 12.

Stereomicroscope 10 has a common objective 14 for a left and a right observation beam path 16L, respectively 16R. Observation beam paths 16L and 16R each contain zoom optics 18L, respectively 18R, which are schematically indicated in FIG. 1 by two lenses 20L, 22L, respectively 20R, 22R.

Observation beam paths 16L and 16R extend into a tube 24, which contains tube lenses 26L and 28L associated with left observation beam path 16L, as well as tube lenses 26R and 28L [sic. 28R] associated with right observation beam path 16R. Moreover, tube 24 has eyepieces 30L and 30R attached thereto which are associated with left observation beam path 16L, respectively right observation beam path 16R.

Stereomicroscope 10, as shown in FIG. 1, further has an image overlay projection device 32, which generates and projects data in the form of light onto a beam splitter 34 disposed in left observation beam path 16L. Beam splitter 34 reflects this light toward tube 24, so that the projected data can be viewed superimposed on the image of the patient's eye 12. Stereomicroscope 10 further includes a video documentation system 36. This video documentation system receives light which strikes a beam splitter 38 disposed in right observation beam path 16R.

An illumination system according to the present invention, which forms part of stereomicroscope 10, will now be described in greater detail. The illumination system includes a light source 38 which directs light through illumination optics 44 including two lenses 40 and 42 and onto a mirror 46, which reflects the light onto an adjustable mirror 48. Adjustable mirror 48 reflects the light onto objective 14, which focuses the light onto the patient's eye 12. The illumination beam path defined by the aforementioned optical components is denoted by 50 in FIG. 1.

As indicated by the double-headed arrow in FIG. 1, adjustable minor 48 is movable along a first portion of illumination beam path 50, which is defined by the reflection of the light by mirror 46 toward adjustable minor 48. In order to achieve such movement, adjustable mirror 48 is coupled to an actuator unit 52.

As shown in FIG. 1, the first portion of illumination beam path 50 extends perpendicularly to a portion of left observation beam path 16L that leads to objective 14. In contrast, a second portion of illumination beam path 50, which is defined between adjustable mirror 48 and objective 14, extends parallel to the aforementioned portion of observation beam path 16L.

The illumination system further includes a refractometer 54, which directs measurement light through refractometer optics 56 onto a beam splitter 58 disposed in right observation beam path 16R. The measurement light emitted by refractometer 54 is directed by beam splitter 58 through zoom optics 18R onto objective 14, which in turn directs the measurement light onto the patient's eye 12.

Refractometer 54 is used for in-situ measurement of one or more optical parameters of the patient's eye. This is accomplished in that the measurement light emitted by refractometer 54 is reflected by the retina of the patient's eye 12 and returned via objective 14, zoom optics 18R, beam splitter 58 and refractometer optics 56 back to refractometer 54, where it is analyzed. In the present exemplary embodiment, refractometer 54 measures a parameter that corresponds to the length of the patient's eye 12, and forwards the same to a control device 60 of the illumination system.

Control device 60 uses the received optical parameter of the patient's eye 12 to determine a control parameter with which actuator 52, which is connected to control device 60, is driven to move adjustable mirror 48. Thus, in the present exemplary embodiment, the control parameter determined by control device 60 corresponds to a control variable which is used to move adjustable mirror 48 from a reference position along illumination beam path 50.

Control device 60 determines the control parameter such that it optimizes the red reflex seen by the operator through eyepieces 30L and 30R. This will be explained later with reference to FIGS. 2A through 2C. The relationship between the parameter of the patient's eye 12 measured by refractometer 54 and the red-reflex-optimized control parameter determined by control device 60 may be established, for example, based on a table which is stored in control device 60 and contains a previously empirically determined correlation between the eye parameter and the control parameter.

In the present exemplary embodiment, control device 60 is also connected to a data processing unit 62 including a keyboard 64 as an input device and a monitor 66 as an output device. Via input device 64, an individual parameter of the patient's eye 12, which is stored in a memory (not shown) provided in data processing unit 60 [sic. 62], may additionally or alternatively be fed to control device 60. Based on this stored parameter, control device 60, in turn, can determine the red-reflex-optimized control parameter.

Figure 2A:
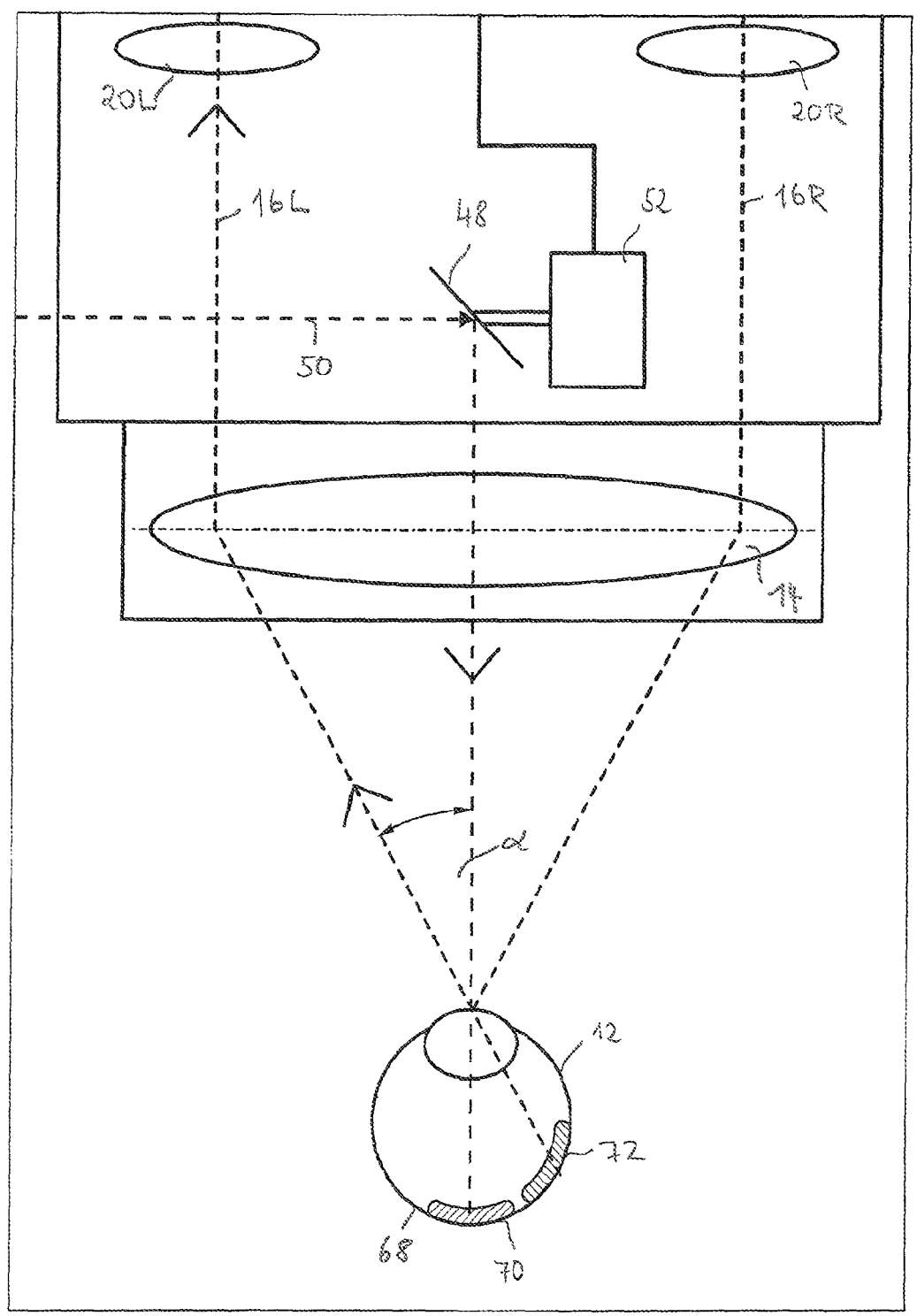
FIGS. 2A, 2B and 2C are enlarged views of a portion of the stereomicroscope of FIG. 1, illustrating how an optical element is moved along an illumination beam path to optimize the red reflex.
Figure 2B:
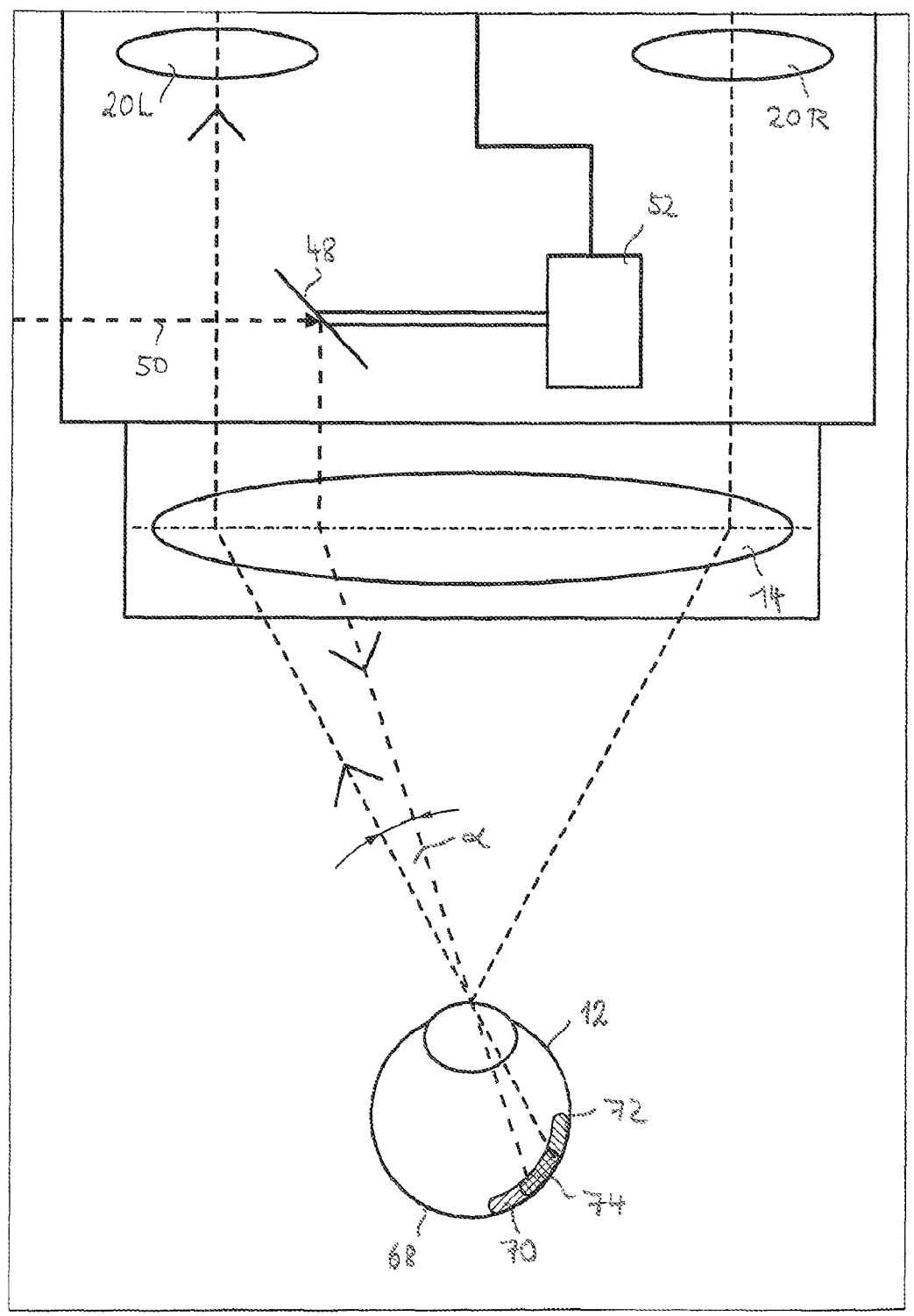
Figure 2C:
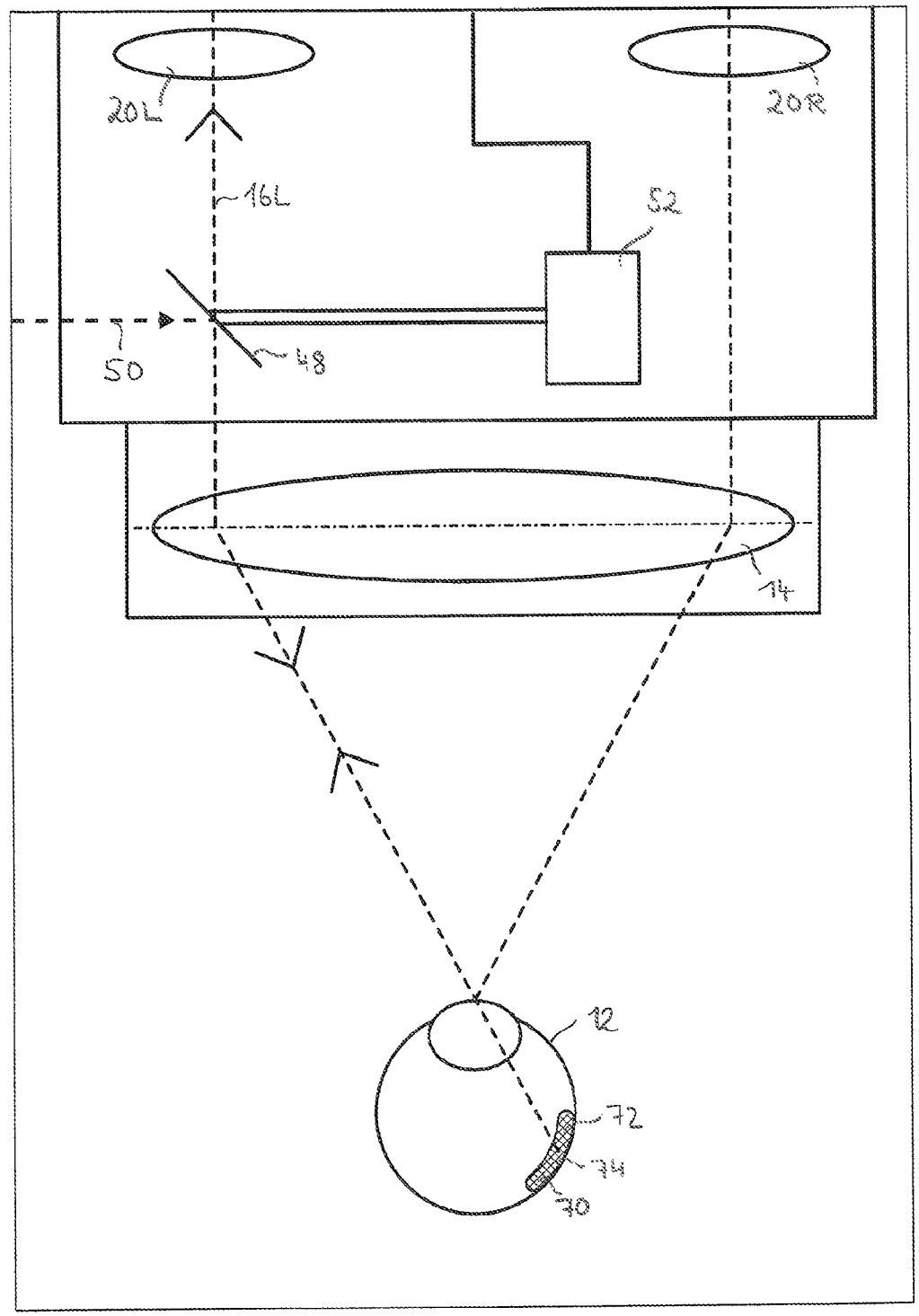

The following illustrates, with reference to FIGS. 2A, 2B and 2C, how adjustable mirror 48 is moved along the first portion of illumination beam path 50 so as to optimize the red reflex seen by the operator.

FIG. 2A shows the initial state, which is also shown in FIG. 1, and in which adjustable mirror 48 is in its reference position. In this reference position, adjustable mirror 48 reflects the light incident thereon onto the patient's eye 12 in such a way that the optical axis of illumination beam path 50 (hereinafter referred to as "illumination axis") is directed perpendicularly to the retina of the patient's eye 12, which is denoted by 68. This illumination produces on retina 68 a light distribution 70, which is also referred to as "illuminated area".

FIG. 2A further shows an observed area 72 on retina 68, which is determined by the orientation of the optical axis of left observation beam path 16L and is hereinafter referred to as "observation axis". In the illumination condition illustrated in FIG. A [sic. FIG. 2A], the illumination axis and the observation axis form an angle at the location of the patient's eye 12, said angle being of a magnitude such that illuminated area 70 and observed area 72 do not overlap on retina 68 of the patient's eye 12. Therefore, no red reflex is produced in this illumination condition.

FIG. 2B shows an illumination condition after actuator unit 52 has moved adjustable mirror 48 closer to the observation axis. As a result, angle between the illumination axis and the observation axis at the location of the patient's eye 12 is reduced, causing illuminated area 70 and observed area 72 to overlap. The overlap region on retina 68 is denoted by 74 in FIG. 2B. This overlap region 74 determines the red reflex seen by the operator.

FIG. 2C illustrates an illumination condition after adjustable mirror 48 has been moved toward the observation axis so that the illuminiation axis and the observation axis coincide. In this illumination condition, the angle shown in FIGS. 2A and 2B is reduced to 0. This results in maximum overlap of illuminated area 70 with observed area 72, and thus, in the maximum possible extent of overlap region 74. Therefore, in addition, the red reflex seen by the operator is optimized.

It will be understood that the mechanics underlying the production of the red reflex are shown in FIGS. 2A through 2C in a simplified schematic form. What is essential in this exemplary embodiment is that it allows adjustable mirror 48 to be moved along illumination beam path 50 according to the control parameter determined by control device 60 and in such a way that the red reflex is optimized Since the parameter of the patient's eye 12, on which the control parameter is based, is measured by refractometer 54 in situ, it is possible for the red reflex to be adapted to the conditions encountered during surgery.

It should be understood that sereomicroscope 10 as shown in FIGS. 1 and 2A, 2B and 2C is merely an exemplary implementation of the present invention. For example, a different optical element, such as a lens or the like, may be used in place of adjustable mirror 48 to adjust the orientation of illumination beam path 50 according to the measured parameter of the patient's eye 12 in order to optimize the red reflex. As mentioned above, it is not absolutely necessary that the optical parameter of the patient's eye 12 be measured in situ using refractometer 54. If suitable data of the patient's eye 12 is available prior to surgery, this data can be fed to control device 60 via keyboard 64, allowing control device 60 to determine the red-reflex optimized control parameter therefrom.

Further, as a safety measure, provision may be made for control device 60 to cause data processing unit 62 to display an enable prompt on monitor 66, requesting the operator to enable adjustment of adjustable mirror 48 according to the control parameter determined by control device 60 in order to optimize the red reflex. The operator may then accept or reject the enable prompt via keyboard 64.

LIST OF REFERENCE NUMERALS

10 stereoscopic ophthalmic microscope
12 patient's eye
14 objective
16L, 16R observation beam paths
18L, 18R zoom optics
20L, 22L, 20R, 22R lenses
24 tube
26L, 28L, 26R, 28R lenses
30L, 30R eyepieces
32 image overlay projection device
34 beam splitter
36 video documentation system
38 beam splitter
40, 42 lenses
44 illumination optics
46 minor
48 adjustable mirror
50 illumination beam path
52 actuator unit
54 refractometer
56 refractometer optics 58 beam splitter
60 control device
62 data processing unit
64 keyboard
66 monitor
68 retina
70 illuminated area
72 observed area
74 overlap region
α angle between the illumination axis and the observation axis

What is claimed is:

1. An illumination system for an ophthalmic surgical microscope (10), comprising
    a light source (32) for emitting light along an illumination beam path (50) directed toward an eye (12) of a patient, and a measuring device (54, 62) for measuring a parameter of the patient's eye (12),
    characterized by an adjustable optical element (48) which allows the orientation of the illumination beam path (50) to be adjusted relative to an observation beam path (16L) of the surgical microscope (10) so as to obtain a red reflex; and
    a control device (60) which determines a red-reflex-optimized control parameter based on the measured parameter of the patient's eye (12) and adjusts the optical element (48) according to the red-reflex-optimized control parameter so as to adjust the orientation of the illumination beam path (50) relative to the observation beam path (16L) of the surgical microscope (10) in order to optimize the red reflex.

2. The illumination system as recited in claim 1,
    wherein the measuring device includes a measuring unit (54) for measuring the parameter of the patient's eye (12) in situ.

3. The illumination system as recited in claim 2,
    wherein the measuring unit (54) is a refractometer.

4. The illumination system as recited in claim 1,
    wherein the measuring device (62) includes an input device (64) for inputting the parameter of the patient's eye (12) that was determined ex situ, as well as a memory unit for storing the parameter that has been input.

5. The illumination system as recited in claim 1,
    wherein the optical element is a mirror (48) disposed in the illumination beam path.

6. The illumination system as recited in claim 5,
    wherein the control device (60) includes an actuator unit (52) which moves the mirror (48) along the illumination beam path (50).

7. The illumination system as recited in claim 5,
    wherein the mirror (48) is positioned in the light-flow direction upstream of an objective (14) of the surgical microscope (10) and divides the optical axis of the illumination beam path (50) into a first portion located in the light-flow direction upstream of the mirror (48), and a second portion located in the light-flow direction downstream of the mirror (48), the first axis portion being perpendicular to an optical axis of the left observation beam path (16L) directed to the objective (14), and the second axis portion being parallel to the optical axis of the left observation beam path (16L) directed to the objective (14).

8. The illumination system as recited in claim 1,
    characterized by an output means (66) for outputting an enable prompt requesting a user to enable adjustment of the optical element (48) according to the determined red-reflex-optimized control parameter, and an input means (64) by which the user enables adjustment of the optical element (48) according to the determined red-reflex-optimized control parameter.

9. An ophthalmic surgical microscope (10) comprising an illumination system according to one of the preceding claims.

10. A method for operating an illumination system for an ophthalmic surgical microscope (10) comprising the following steps:
    emitting light along an illumination beam path (50) directed toward an eye (12) of a patient;
    measuring a parameter of the patient's eye (12);
    determining a red-reflex-optimized control parameter for an adjustable optical element (48) of the illumination system based on the measured parameter of the patient's eye (12), said adjustable optical element allowing the orientation of the illumination beam path (50) to be adjusted relative to an observation beam path (16L) of the surgical microscope (10) so as to obtain a red reflex; and
    adjusting the optical element (48) according to the red-reflex-optimized control parameter so as to adjust the orientation of the illumination beam path (50) relative to the observation beam path (16L) of the surgical microscope (10) in order to optimize the red reflex.

* * * * *